US006668388B2

(12) United States Patent
Buttigieg (10) Patent No.: US 6,668,388 B2
(45) Date of Patent: Dec. 30, 2003

(54) RETRACTABLE AND DISPOSABLE URINAL (75) Inventor: Carmel Buttigieg, Santa Venera (MT)

(73) Assignee: Yamamoto Limited, Valletta (MT)

( * ) Notice: Subject to any disclaimer, the term of this patent is extended or adjusted under 35 U.S.C. 154(b) by 0 days.

(21) Appl. No.: 10/234,804

(22) Filed: Sep. 4, 2002

(65) Prior Publication Data

US 2003/0046753 A1 Mar. 13, 2003

(30) Foreign Application Priority Data

Sep. 10, 2001 (MT) ................................................ 1636

(51) Int. Cl.⁷ .............................................. A47K 11/12
(52) U.S. Cl. ...................... 4/144.2; 4/144.3; 604/349; D24/122
(58) Field of Search ............................... 4/144.2, 144.3, 4/144.1, 144.4; 604/349; D24/122

(56) References Cited

U.S. PATENT DOCUMENTS 3,956,778 A * 5/1976 Tanaka ....................... 4/144.1
4,531,245 A * 7/1985 Lowd et al. ................. 4/144.3
4,994,051 A * 2/1991 Walsh ......................... 604/349
5,007,116 A * 4/1991 Yamamoto ................... 4/144.2
5,295,983 A * 3/1994 Kubo ....................... 4/144.3 X
6,059,762 A * 5/2000 Boyer et al. ................. 604/349
6,186,990 B1 * 2/2001 Chen et al. .................. 604/349
6,202,224 B1 * 3/2001 Freeman ..................... 4/144.2
6,248,096 B1 * 6/2001 Dwork et al. ............... 604/349

FOREIGN PATENT DOCUMENTS

GB          2099297       * 12/1982 ................. 4/144.1

* cited by examiner

Primary Examiner—Gregory Huson
Assistant Examiner—Kathleen J. Prunner
(74) Attorney, Agent, or Firm—Bucknam and Archer (57) ABSTRACT A retractable and disposable urinal which can be retracted, can be directed and can be joined with a plastic conveyer to the male or female organ and comprises: a plastic retractable tube formed by a plurality of convolutions, having at its bottom a closed convolution and at its top a hollowed neck closed at its bottom side where an absorber polymer is put, the conveyer entering the neck opens the protection film and the membrane of the neck allowing the polymer to fall down the tube, this polymer when is in contact with the urine absorbs it and transforms it in gel.

11 Claims, 7 Drawing Sheets

RETRACTABLE AND DISPOSABLE URINAL

BACKGROUND OF THE INVENTION

The problem of urine-emergency borns when someone can not move normally his body and therefore needs an urinal. Up today a lot of solutions exit on the market in order to solve this problem generally focused to avoid the traditional urinal and to be a disposable product.

Figure 1:
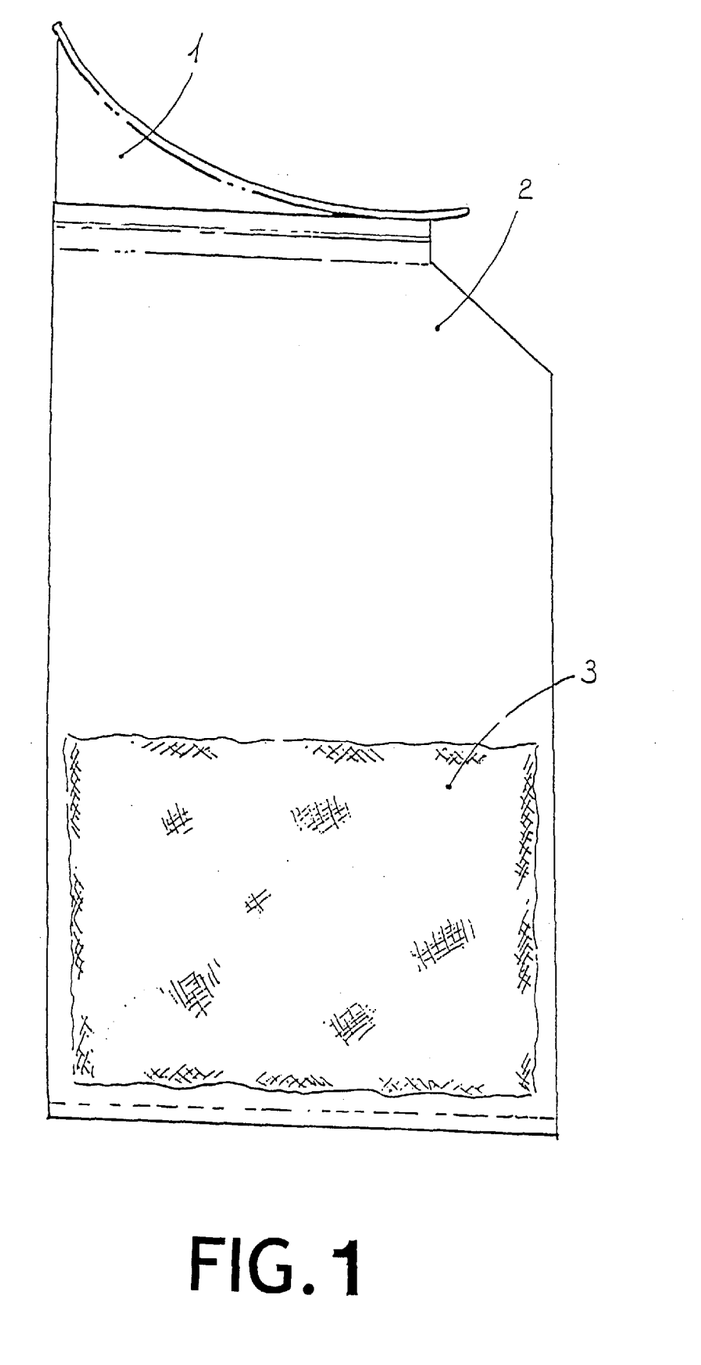
FIG. 1 is a front view of a disposable urinal according to the prior art.

All these solutions are basically formed by three parts, as shown in FIG. 1:

An unisex plastic conveyer (1),
A storage plastic bag (2),
A pouch (3) filled with an absorbing polymer.
Why these products work badly.

The solderings made on the plastic bag between the two layers and between the bag with the conveyer, being made manually, sometime are not perfect causing a possible dripping.

The difficulty to direct down the bag when the user is bedridden.

The pouch with the absorber polymer being very sensitive to the humidity loses its property very soon specially if stored where the moisture in the air is high.

The reaction time of the polymer is prolonged by the barrier effect of the material used for the pouch, generally paper or non-woven fabric, which, under the influence of the expansion pressure has to be broken into fragments dispensing the polymer, it means time which, in that moments, the user has not.

In case of a recycling, the present disposable urinals have some problems because formed by two different components and the expulsion of the urine become gel is difficult because is amalgamated with the fragments of the pouch. Another aspect to be considered is the production cost.

The present disposable urinals are constructed manually making these operations:

The plastic bag has to be soldered at its top in order to give it an inclination, The conveyer has to be soldered to the plastic bag, The pouch (produced on another line) with the polymer has to be inserted into the bag, The whole product has to be folded and inserted into an another plastic bag, which also has to be soldered.

It is calculated that for these operations, which are totally manual, the required time is more than one minute.

For a disposable product all these costs have to be avoid. Another aspect to be considered as background of this invention is the use of this invented urinal also for incontinence and as substitute of the catheter.

SUMMARY OF THE INVENTION

The crux of the present invention is to make a retractable and disposable urinal having the following characteristics:

Easy to handle,
Easy to direct,
Easy to recycle,
Low volume when stored,
No pouch filled with absorbing polymer,
Reaction time of the absorber polymer very fast,
Low production cost.

In order to reach these characteristics the urinal will be made as shown in FIG. 2—FIG. 3—FIG. 4—FIG. 5—FIG. 6, where:

Figure 2:
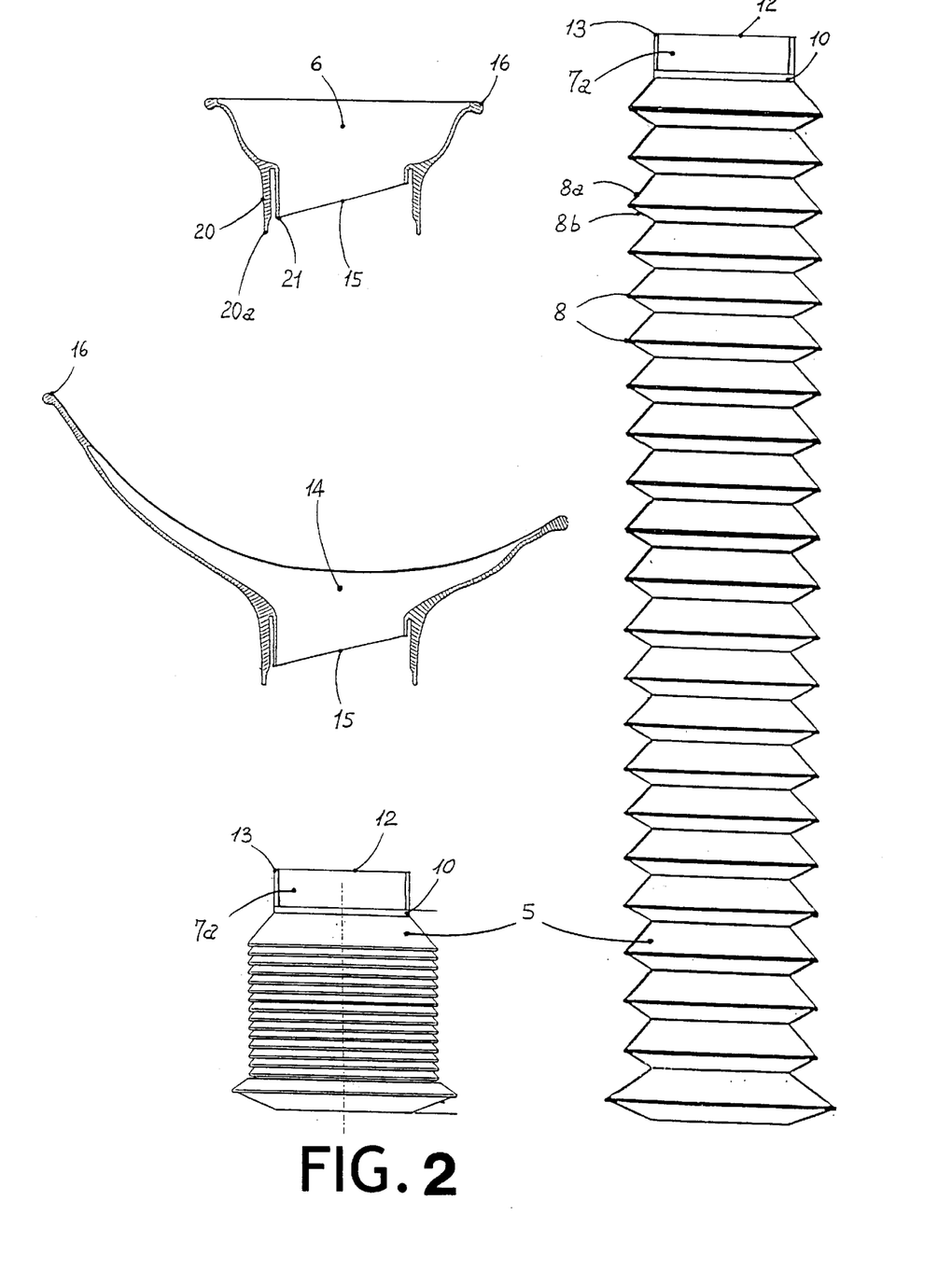
FIG. 2 is a front view of the urinal of the present invention, as in the case of its extension -A-, as in the case of its compression -B- and the cross section of the male (6) and female (14) conveyer.

As shown in FIG. 2 the tube, whose role is the urine storage, is formed by a plurality of convolutions (8) made with an upper ring (8a) bigger than the lower ring (8b) in order to enter easily each other under a compression of the whole tube.

The tube has at its bottom a closed convolution (9) with a bigger diameter. At the opposite side of the tube a hollowed closed neck (7a) is made whose role is to store and to keep dried the absorber polymer (4), its external ring (11) is close with a plastic film (12) soldered to its edge (13a).

The tube (5) is produced with the process of the blowing moulding using a mould whose internal figures correspond to its maximum extension FIG. 2A. Being the tube (5) long enough to store a complete miction the polymer, when put inside, falls down at its bottom side. In this case the property of an immediate gelatinizing is reduced because the urine gelatinzes the exposed surface but internally does not work. For this reason, when the process of blowing is made also an essential oil will be blowed inside the tube. With this operation the polymer will adhere around the whole internal surface of the tube and progressively will gelatinize the urine.

Once the tube is produced falls into a assembling line where these operations are made:

Compression of the tube (5),
Inserting of the polymer (4) into the neck (7a),
Soldering of the film (12) on the edge (13a) of the neck,
Falling into the final packaging.

The production of this kind of urinal does not forecast any manual operation because made in a proper assembling line and therefore its production cost is very low.

Figure 4:
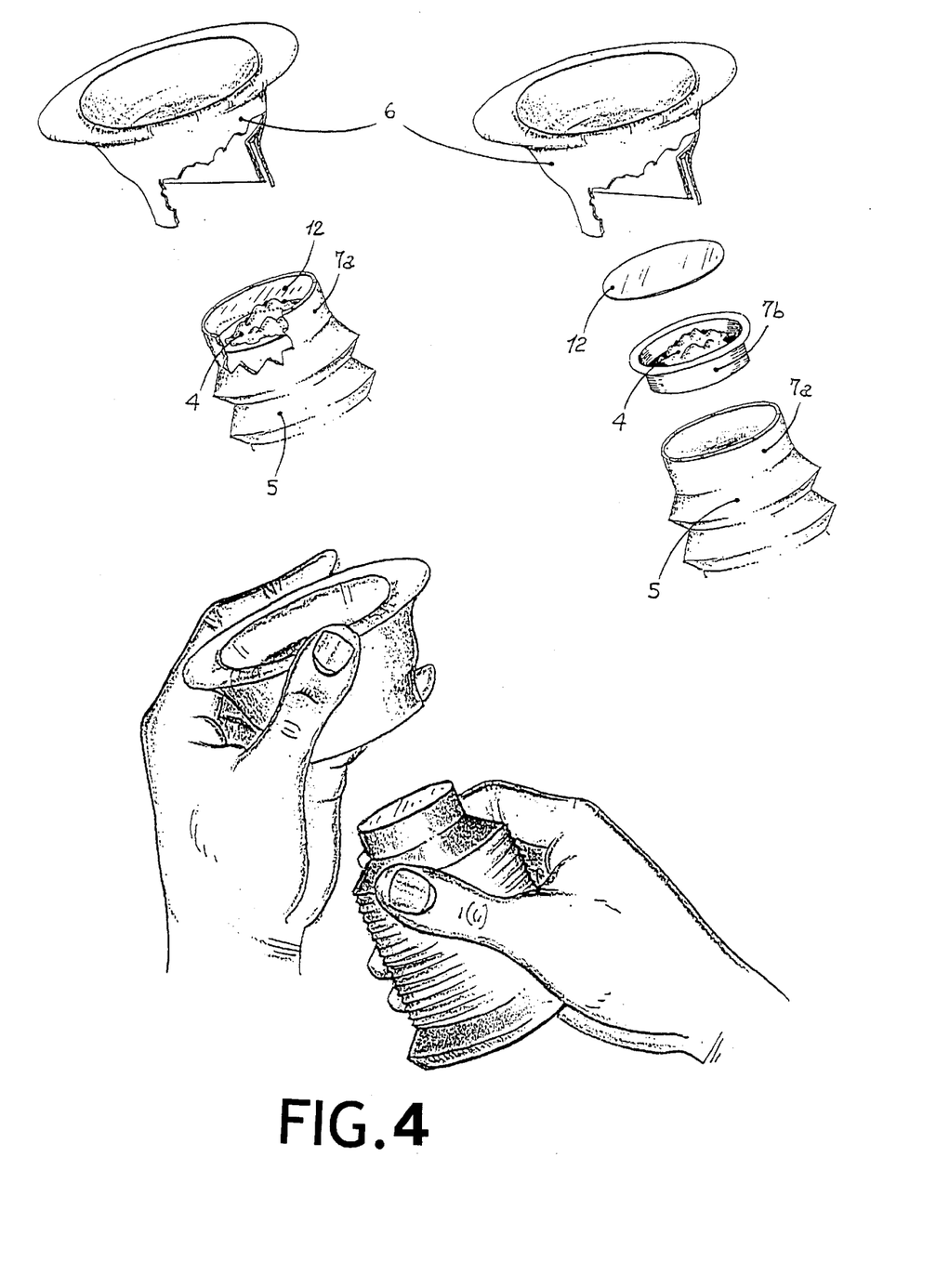
FIG. 4 shows the operations made by the user for a proper use of the urinal and a special cap (7b) capsulized into the preformed neck (7a).

As shown in FIG. 4 instead of the filling of the tubers neck (7a) with the polymer, a cap (7b), which is filled with the polymer, can be produced. This cap, once filled with the polymer will be covered by the same film (12) soldering it on its edge (13b), obviously this cap will be inserted into the neck (7a) which, in this case, is not closed but totally open.

Figure 5:
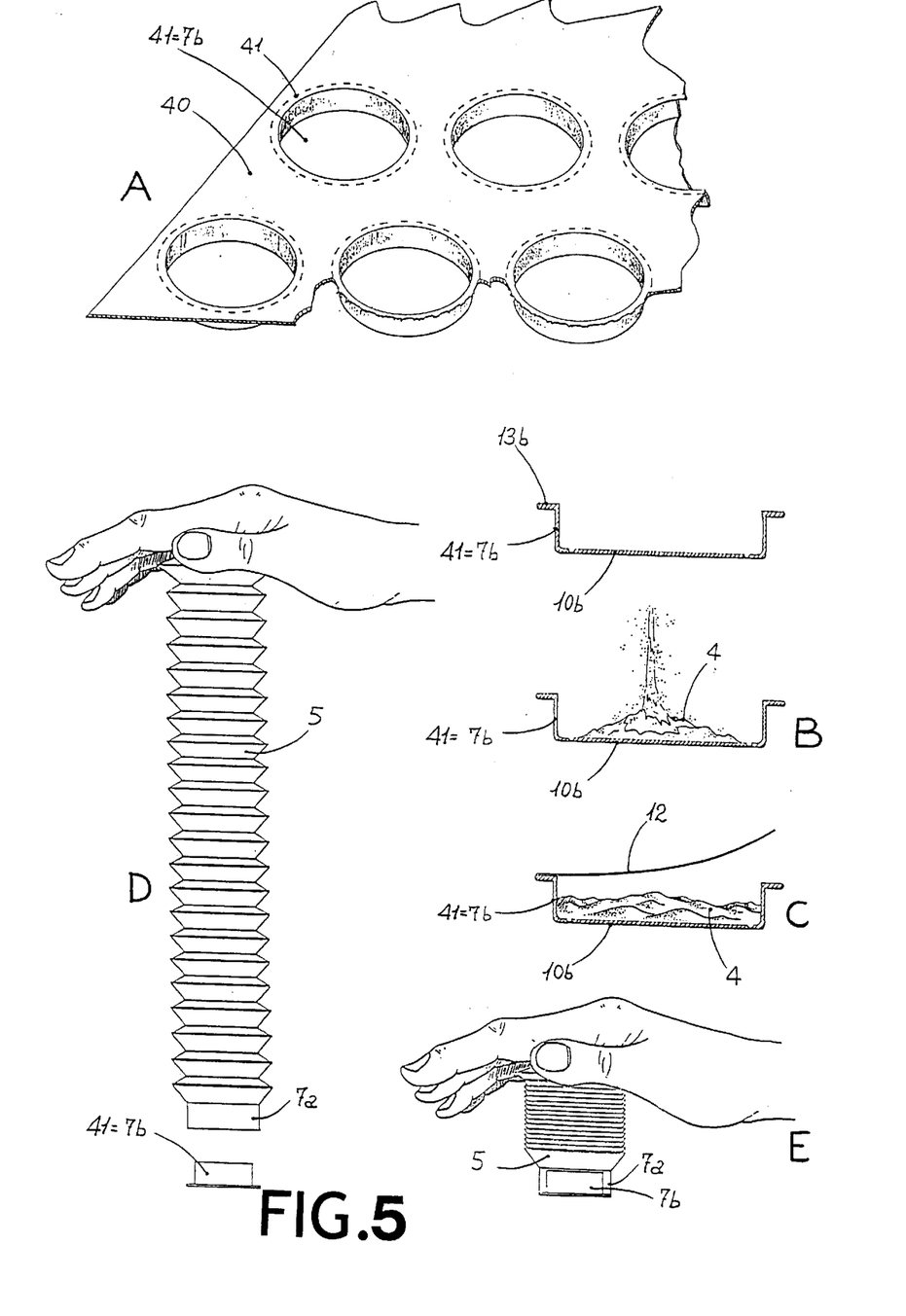
FIG. 5 shows the production of a plurality of caps (7b) with the process of the vacuum forming and its insertion into the neck.

The FIG. 5 shows how this cap is produced. It can be produced with the process of the injection moulding but this invention forecasts the production with the process of the vacuum forming for the following reasons.

This cap has to be very thin,
It must have a big productivity,
It must have a perforated edge in order to allow a perfect wrench.

The vacuum forming process starts from thiny sheets or from rolls of rigid plastic material (A) the used moulds have a plurality of figures (41), the plastic material is softened by an oven and sucked into the figures, after is cooled by compressed air or by ventilators. In this case a tray incorporating a lot of caps is formed. After this tray passes through a press which perforates the edge of every cap formed into the tray.

The tray so obtained is put in an assembling line where the following operations are made.

(B) The filling of the polymer (4),
(C) The soldering over the whole tray of a plastic film (12), after this soldering, and in the same station of the line, the edge of every cap is perforated (42), (D) The insertion of each single neck (7a) of the extended tube (5) into each single cap (7b),
(E) The compression of each single tube.

After this operations which are done in a proper assembling line, the tray is full of single urinals compressed into the caps and ready for the use. In other lines the male (6) and female (14) organ conveyers are made. They are produced with the process of injection moulding.

As shown in FIG. 2 both these conveyers have these characteristics:

A specific fitting to the specific organ,
A bottom side which has internally an inclinated tube made like a spout (15),
A top side made with an enlarged edge (16).
How these urinals are used.
a—First application for bedridden patients,
b—Second application for incontinents.

In the first application the male-female conveyer has to be produced with a hard plastic material as polyethylene or polypropylene, in the second one it has to be produced with a soft material as latex or polyurethane or thermoplastic rubber or similar, because incontinents may stand on during the day and can have the urinal adhering to the genital area for some hours.

The tube is the same for both these cases, eventually for standing patients this tube can have a smaller diameter and a bigger length, in order to have a similar volume which is more than 500 milliliter.

For both these applications the use is shown in FIG. 4 where:

Firstly the user takes the conveyer (in the drawing it is shown the male one) in a hand (A) and in the other hand (B) the compressed tube, which, as referred, contains into its neck (7a) the absorber polymer sealed by a film (12) soldered around its edge (13). After the user inserts the conveyer into the neck.

This insertion is easy because the shape of the inserting tube of the conveyer which has a double arms (20–21) for entering and for holding the edge of the neck, the beginning is facilitated because the bottom side of the conveyer is enlarged (20a), as shown in FIG. 2.

Figure 3:
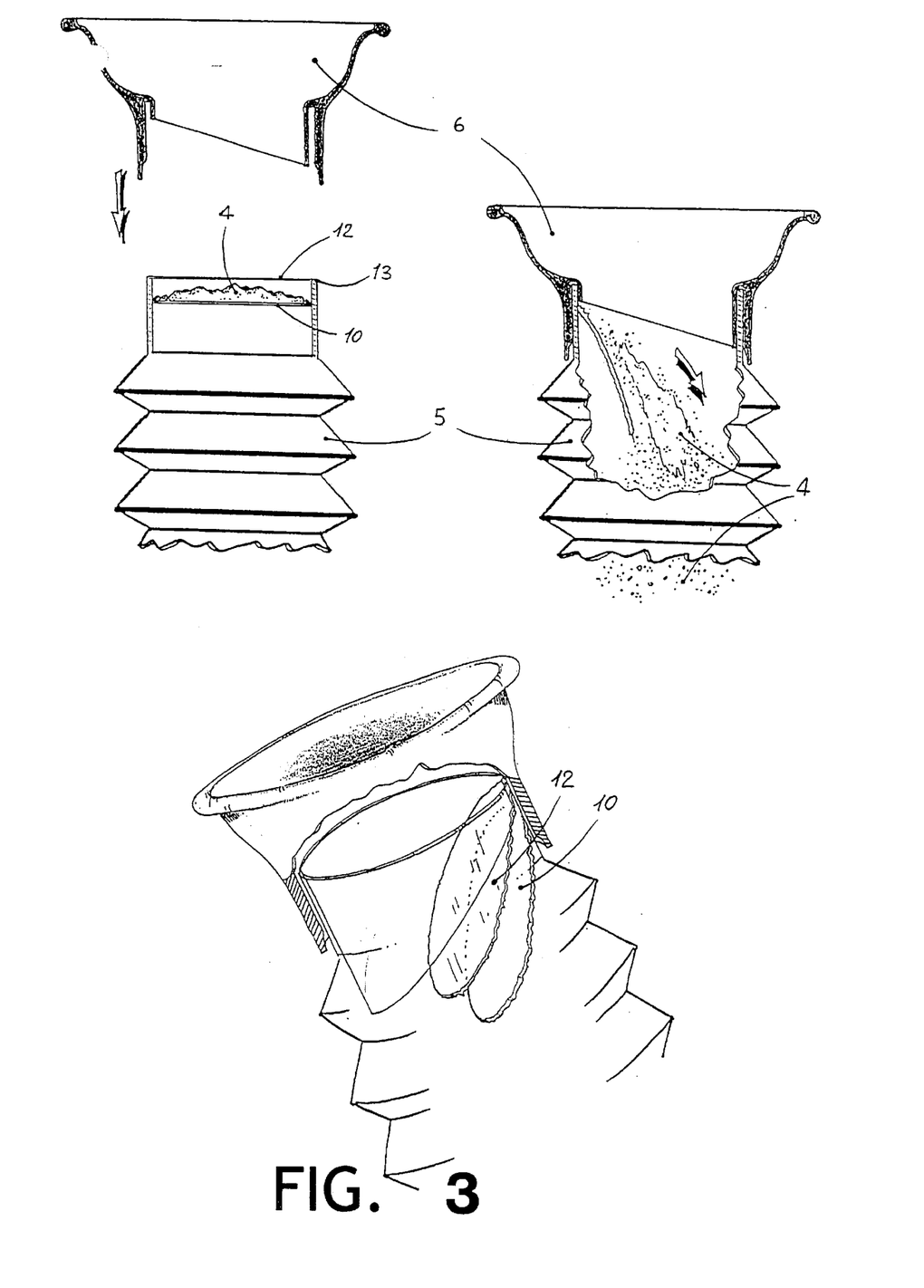
FIG. 3 shows the joint of the tube (5) with the male conveyer (6).

The spout (15) enters progressively the neck cutting the film (12) and the membrane (10) supporting the absorber polymer and allowing it to fall down the tube (5), this parts (12–10) are partially cut because the shape of the spout and therefore remain in the position as a hinge obtaining the following results: the organ does not touch the polymer because the protection of the film (12) and the urine does not drip out because the barrier effect of the membrane (10) as shown in FIG. 3.

In this case this polymer will work in the best condition being free internally the tube and not incapsulated or fixed into layers of papers or non-wollen fabrics as all the other applications in the market and its reaction time is very fast.

The nature of the absorber polymer can vary and consequently also the reaction time can vary. The most important polymers for this purpose are:

Cellulose-acrylonitrile—Carboxymethylated polysaccharide acrylonitrile and in general all the by-products of the polyacrilic acid and of the polyacrilonitrile Also a natural component can be used for gelatinizing the urine: the dried and pulverized algas even if, in this case, the reaction time is prolonged.

Figure 6:
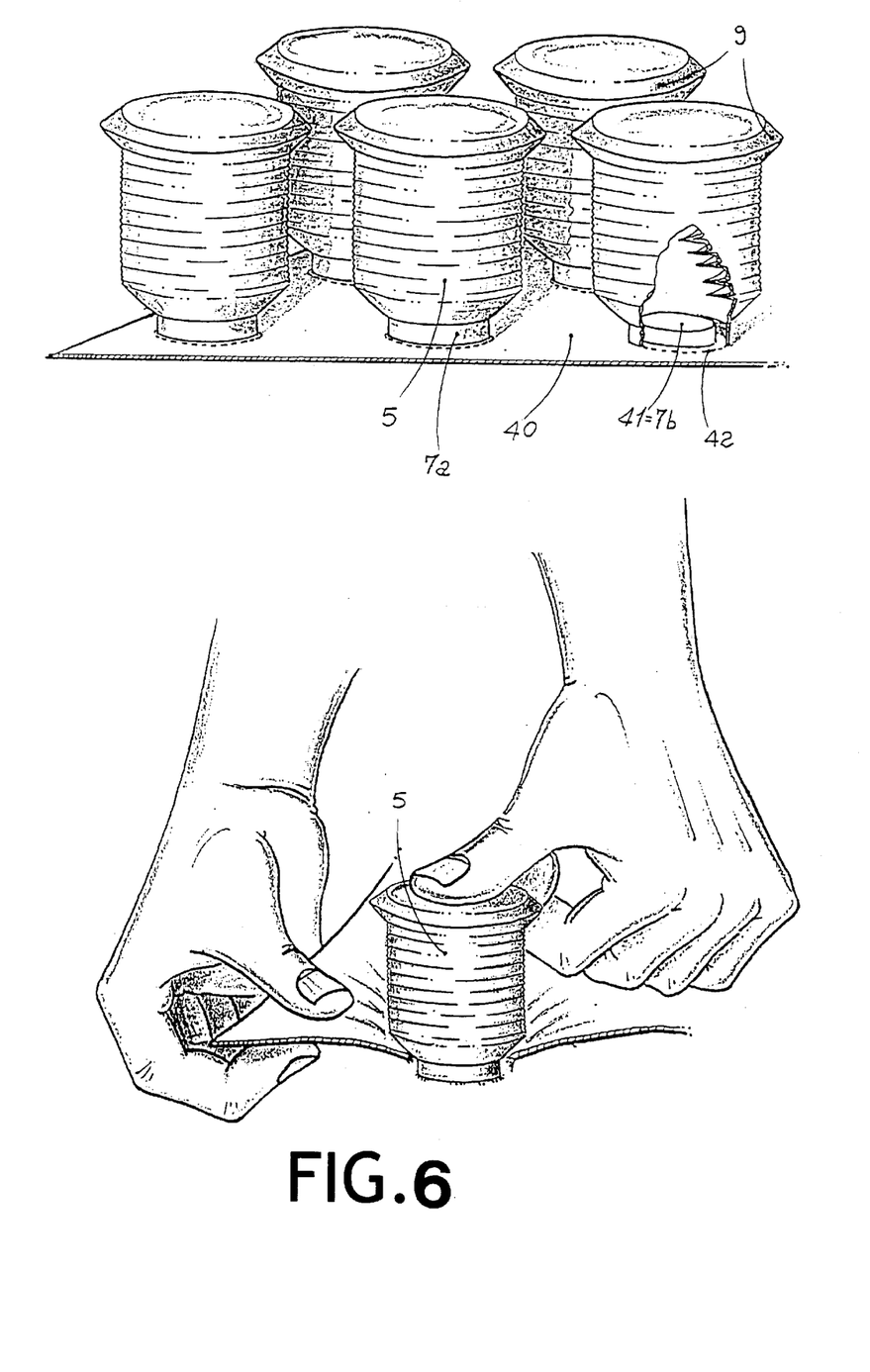
FIG. 6 shows the action for taking away the compressed tube (5) from the tray
Figure 7:
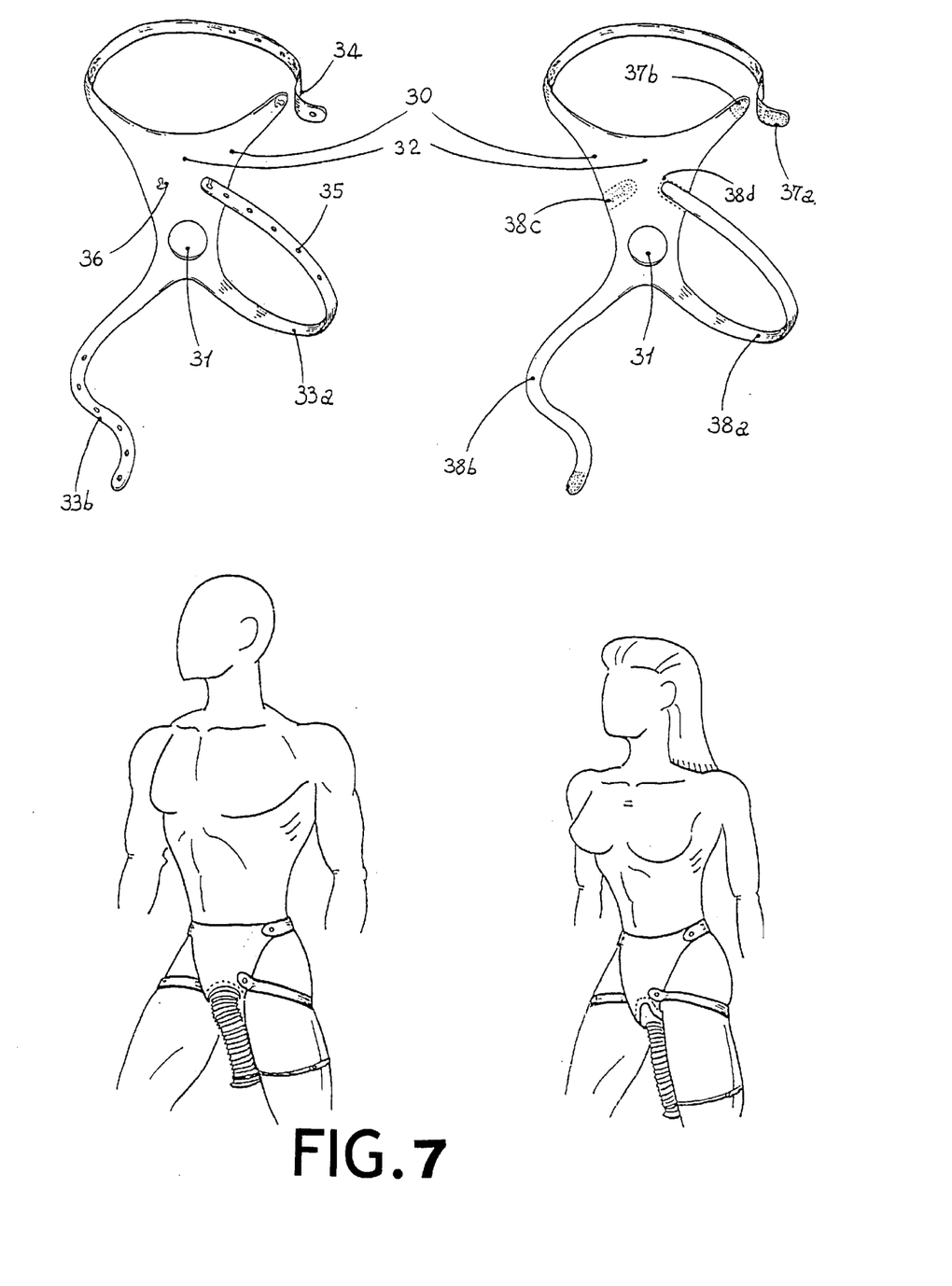
FIG. 7 shows the application of this urinal for incontinents.

The second application of this invention, as shown in FIG. 6, is the use of this urinal for incontinence.

The present invention can solve this problem because is essentially a retractable tube which can enter the hole (31) formed on the device (30) properly made for this purpose and its use is quite simple. Basically it is a suspensory bandage formed by a front part (32), which is in contact with the belly, and by three belts: the lower ones, right (33a) and left (33b), wind round the corresponding legs, the upper one (34a) winds round the waist.

Once the tube (5) of the invented urinal is inserted into the hole (31) and is directed down along the legs, is kept in the right position because the male or the female conveyer and their enlarged edge (16) can not pass through the hole and are in the right position for keeping the male or female organs because are pressed by the suspensory belts whose adhering force can be regulated because its closing system.

This closing may be made in two ways.

The first way to fasten the belts is inserting the pins (36), which are sewed or glued to specific points in the front part (32), into one of the holes (35) giving the user the best feeling of tightness.

The second way to fasten the belts is the use of the detachable products known with the commercial names of Velcro or magic tape, also in this case the suspensory has three belts: the lower ones, right (38a) and left (38b) wind round the corresponding legs and will be joined to the Velcro (38c–38d) and the upper one (37b) winds round the waist and will be joined to the Velcro (37a).

This application can be made also wearing normal underpants on which a hole is formed which allows the end of the tube (5) but not the exit of the conveyer. It is clear that in this case the conveyer of male-female organ has not a perfect adhesion as with the suspensory.

For this reason this invention can partially substitute the external catheters and the concerning urine-collecting bags.

Another aspect is to be considered.

The retractable tube (5) being formed by a plurality of convolutions can make a bellows-effect. If the user compresses and leaves the tube, as a pump, when the urinal is in the right position adhering perfectly to the genital area, the tube can suck the urine in those patients suffering of lack of miction, avoiding, in some cases, the use of the bladder catheters.

What is claimed is:

1. A retractable and disposable urinal formed by a conveyer of the male (6) and the female (14) organs inserted into a urine-storage container which is a retractable tube (5) formed by a plurality of convolutions (8) of which the last one located at the tube's bottom (9) has a bigger diameter than the other ones and the first one located at the tube's top is a cave neck (7a) closed at its bottom by a membrane (10a) where internally an absorber polymer (4) is put, the neck is closed at its top with a plastic film (12) soldered around its edge (13a), said neck instead of closed by the membrane can be open allowing the entering of a special cap (7b) which is filled with the absorber polymer (4) and closed with the plastic film (12), said retractable tube has the property to be inclinated in all the directions, said absorber polymer has the property to gelatinize very fast the urine and is a product already used for this kind of purposes as the sanitary napkin.

2. A retractable and disposable urinal, according to claim 1-where the retractable tube (5) is produced with the process of the blowing moulding using a mould whose internal figures correspond to its maximum extension, when the process of blowing is made also an essential oil is blowed inside the tube because with this operation the polymer will adhere around the whole internal surface of the tube and progressively will gelatinize the urine, said tube is compressed in an assembling line, properly made, where also the following operations are made: inserting the polymer into the neck (7a) and soldering the film (12) over the edge (13a) of the neck.

3. A retractable and disposable urinal according to claim 1-where the absorber polymer, instead of inserted into the closed neck (7a) is inserted in a special cap (7b) which will be sealed by a plastic film (12), said cap is produced with the process of the vacuum forming starting by a sheety or by a roll of rigid plastic film, the mould has a plurality of cavities with the exact shape of the plurality of caps in order to produce a tray with a plurality of caps, said tray is put on a line which provides to fill all the caps with the polymer, to solder the sealing film (12) to the whole tray, to perform the edge of each single cap (41), to compress each single tube.

4. A retractable and disposable urinal according to claim 1-where the conveyer of the male (6) and the female (14) organs are produced with plastics with the process of the injection moulding, said conveyer has a specifying fitting to the specific organ, said conveyer has a top side made with an enlarged edge (16) and a bottom side which has internally an inclinated tube made like a spout (15), said spout cuts the external protection film (12) and the internal membrane (10), said film and said membrane remain in the position as a hinge being cut nor completely, said film protects the organ, said membrane makes a barrier effect to the urine.

5. A retractable and disposable urinal according to claim 1-which is packed in a proper assembling line, said urinal has a very little volume when the retractable tube is compressed, said urinal does not suffer the humidity because the absorbing polymer (4) is kept dried being incapsulated into the neck (7a) or into the cap (7b) protected by the film (12).

6. A retractable and disposable urinal according to claim 1-which once used can easily washed and recycled because formed by a retractable tube and a conveyer of organs made with the same plastic material.

7. A retractable and disposable urinal according to claim 1-where instead of an absorber chemical polymer (4) which has the property to gelatinize very fast the urine, natural components can be used as the dried and pulverized algas.

8. A retractable and disposable urinal according to claim 1-which, with an appropriate device, can be used for incontinent patients, because is essentially a retractable tube (5) entering the hole (31) formed on the front part (32) of a special suspensory bandage (30) and by, at least three belts of which two wind around the legs (33a–33b) and one around the waist (34a), said belts are fixed to the font part (32) by a system of pins (36) fixed on the front part and holes (35) preformed on the belts or by the Velcro fastener (37a–37b), said tube does not move out of the hole because the enlarged edge of the conveyer (6–14) can not go out from the hole (31) and the closing systems allow a perfect fitting to the genital area.

9. A retractable and disposable urinal according to claim 1-which can be used by incontinent patients wearing normal underpants on which a hole is formed on the genital area, said hole allows the exit of the tube (5) but does not allow the exit of the conveyer.

10. A retractable and disposable urinal according to claim 1 which is a valid substitute of the external catheter and the concerning urine-collecting bag because the retractable tube (5) for a better use is fixed to a leg by a string.

11. A retractable and disposable urinal according to claim 1 which is a valid substitute of the bladder catheters and the concerning urine-collecting bag because the retractable tube (5) being formed by a plurality of convolutions makes a bellows-effect because if the user compresses and leaves the tube, as a pump, when the urinal is in the right position adhering perfectly to the genital area, said tube sucks the urine in those patients suffering of lack of miction.

\* \* \* \* \*